United States Patent [19]
Sakon et al.

[11] Patent Number: 5,972,388
[45] Date of Patent: *Oct. 26, 1999

[54] ULTRAFINE PARTICLE POWER FOR INHALATION AND METHOD FOR PRODUCTION THEREOF

[75] Inventors: Kiyoyuki Sakon; Masahiro Sakagami; Yuji Makino; Yoshiki Suzuki; Hideki Kobayashi, all of Hino, Japan

[73] Assignee: Teijin Limited, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/779,614

[22] Filed: Jan. 7, 1997

Related U.S. Application Data

[63] Continuation of application No. 08/193,181, filed as application No. PCT/JP93/00786, Feb. 12, 1993, abandoned.

[30] Foreign Application Priority Data

Jun. 12, 1992 [JP] Japan ................................. 4-153538
Aug. 12, 1992 [JP] Japan ................................. 4-215133

[51] Int. Cl.⁶ ............................... A61K 9/14; A61K 9/72; A61K 47/38
[52] U.S. Cl. ......................... 424/499; 424/489; 424/46; 514/781; 514/951; 514/958
[58] Field of Search ................. 424/489, 499, 424/46; 514/951, 958, 169, 821, 826, 850, 781

[56] References Cited

U.S. PATENT DOCUMENTS

| | | | |
|---|---|---|---|
| 4,294,829 | 10/1981 | Suzuki et al. | 424/47 |
| 4,414,209 | 11/1983 | Cook et al. | 514/958 |
| 4,462,983 | 7/1984 | Azria et al. | |
| 4,590,206 | 5/1986 | Forrester et al. | 514/951 |
| 4,804,678 | 2/1989 | Augstein et al. | 424/450 |
| 4,917,897 | 4/1990 | Augstein et al. | 424/450 |
| 5,260,306 | 11/1993 | Boardman et al. | 514/291 |
| 5,290,540 | 3/1994 | Prince et al. | 514/958 |
| 5,641,510 | 6/1997 | Clark et al. | 424/451 |
| 5,747,445 | 5/1998 | Backstrom et al. | 514/4 |
| 5,830,853 | 11/1998 | Backstrom et al. | 514/4 |

FOREIGN PATENT DOCUMENTS

| | | |
|---|---|---|
| 0023359 | 2/1981 | European Pat. Off. . |
| 0193372 | 9/1986 | European Pat. Off. . |
| 0257915 | 3/1988 | European Pat. Off. . |
| 0504760 | 9/1992 | European Pat. Off. . |
| 2851489 | 5/1979 | Germany . |
| 5620509 | 2/1981 | Japan . |
| 5732215 | 2/1982 | Japan . |
| 2193891 | 2/1988 | United Kingdom . |
| 9110434 | 7/1991 | WIPO . |
| 9111179 | 8/1991 | WIPO . |

OTHER PUBLICATIONS

Bioadhesive Drug Delivery Systems, CRC Press, Inc., Vincent Lenaerta, Ph.D. et al, pp. 175–176.

Keller, "Pharmazeutische Aerosole Eigenschaften, Anforderungen, FCKW–Umweltproblematik und Moegliche Alternativen", *Deutsche Apotheker Zeitung*, 131(7):263–269 (1991).

"Workshop on Medical Aerosol", *Medical Way*, 1(9):158–159 (1984).

"Guide to Use of Omron Nebulizer", *Omron Nebulizer*, pp. 5–6 (Dec. 1, 1989).

M. Vidgren et al., Drug Development and Industrial Pharmacy, 18(5), 581–597, 1992, 6$^{th}$ International Conference on Pharmaceutical Technology, Paris June 2–4, 1992.

*Primary Examiner*—Robert H. Harrison
*Attorney, Agent, or Firm*—Sughrue, Mion, Zinn, Macpeak & Seas, PLLC

[57] ABSTRACT

An ultrafine particle powder for inhalation to be delivered mainly to a lower airway, containing specific cellulose lower alkyl ethers and a medicament, at least 80% of the powder having a particle size in the range of 0.5 to 10 μm.

8 Claims, 5 Drawing Sheets

ULTRAFINE PARTICLE POWER FOR INHALATION AND METHOD FOR PRODUCTION THEREOF

This is a Continuation of application Ser. No. 08/193,181, filed Feb. 14, 1994, now abandoned which is a 371 of PCT/JP93/00786 filed June 11, 1993.

TECHNICAL FIELD

The present invention relates to an ultrafine particle powder for inhalation, and a method for the production thereof. The present invention relates in more detail, to an ultrafine particle powder for inhalation comprising a specific cellulose lower alkyl ether and a medicament, at least 80% of said powder having a particle size of 0.5 to 10 $\mu$m, a method for the production thereof, and a powder preparation for inhalation comprising the same.

BACKGROUND ART

An inhalant is a preparation intended to be administered as a medicament from an oral cavity or nasal cavity mainly to a lower airway such as a trachea, bronchi and alveoli. A lower airway, of an airway, is defined herein as a trachea, bronchi, bronchioles, alveoli, etc.

Inhalants are expected to target organs, to act as preparations for local administration to thoracopathy such as asthma, bronchitis and pulmonary emphysema of medicaments, and to relieve side effects and realize quick efficacy on the basis of the targeting, and many of them have already been practically used. Much attention has recently been drawn to inhalants as medicaments to be generally administered to transfer physiologically active peptides, proteins, etc., from alveoli to a blood stream (V. H. L. Lee, "Peptide and Protein Drug Delivery," Marcel Dekker, 1991, pp. 1–56). Furthermore, vaccine preparations such as an influenza vaccine have also been tried to induce local immunity by inhalation of an antigen.

Such inhalants can be classified as follows according to a state of the particles depositing within an airway: (1) a solution depositing as droplets; and (2) an aerosol or powder depositing as powder. A solution is usually an aqueous solution of a medicament. It is formed into mist by a nebulizer, (or atomizer) and administered to within an airway as minute droplets, thereby depositing within the airway in the form of droplets. On the other hand, in the case of aerosol, a medicament is usually filled in a pressurized container in the form of a dispersion or solution in fluorohydrocarbon. When the aerosol is released therefrom at the time of administration, fluorohydrocarbon is gradually vaporized, and the dispersed or dissolved medicament gradually becomes a fine particle powder, which finally deposits within the airway as a fine particle powder. Moreover, in the case of a powder, a fine particle powder containing a medicament is filled as a powder in a container such as a hard capsule. A patient usually inhales it as powder mist therefrom by patient's own inspired air through a suitable medicator, and the fine particle powder itself deposits within the airway.

Desirable properties of the inhalants can be classified as follows, by aspects of medicament efficacy and by aspects of physical chemistry.

Firstly, with regard to aspects of medicament efficacy, since an airway has a complicated and narrow structure, the medicament is required to be delivered to a target site therewithin efficiently and deposited. Delivery of the medicament to target sites such as a trachea, bronchi, branchioles and alveoli and deposition thereof at the target sites require participation of many factors such as a particle size; properties of the particles, e.g., density, shape and electric charge; a concentration of the mist, a particle size distribution and respiration patterns (see, for example, V. H. L. Lee, "Peptide and Protein Drug Delivery," Marcel Dekker, 1991, p. 10 mentioned above). However, of these factors, the most important one is a particle size. Since the relationship between a particle size and a delivery site differs depending on researchers, it is not absolute. However, an example of the relationships is as follows: particles having a size of 10 $\mu$m or more are trapped within on oral cavity and nasal cavity, and deposited there; they are required to have a size of approximately 5 to 15 $\mu$m to be delivered to a trachea and bronchi, and deposited there; they are required to have a size of approximately 2 to 5 $\mu$m to be delivered to bronchioles, and deposited there; there are required to have a size of approximately 0.3 to 2 $\mu$m to be delivered to alveoli, and deposited there (report from "Workshop on Medical Aerosol").

After a comprehensive review of other reports, it may be concluded that for the purpose of efficiently delivering a medicament to a site deeper than a trachea, namely, to a lower airway and depositing it there, it desirably has a particle size in the range from 0.5 to 10 $\mu$m.

Secondly, since the surface of an airway such as a trachea and bronchi is covered with a mucosa, the airway is a very sensitive organ, a preparation should therefore be non-irritative. Additives and residual solvents which may injure the mucosa should be avoided as far as possible.

Thirdly, it is desirable that a medicament is retained at a target site within the airway for a time sufficient to realize its action. An epidermis within the airway has cilia, which move in such a way that inhaled foreign materials are moved to the esophagus. Accordingly, in order to display the efficacy thereof, it is desirable that the medicament is not readily moved by cilia and retained at the site to be deposited. Sustained release of the medicament while it is retained further enhances its efficacy.

For example, in the case of a treatment for asthma, disodium cromoglycate requiring frequent administration and steroids whose dose is desired to be decreased from the standpoint of safety become significantly useful when they are formulated to sustained action preparations requiring a decreased number of administration and a decreased amount of dose. Moreover, in the case of administering a physiologically active peptide protein, a preparation thereof intended to improve mucosa-adhesivity or mucosa-staying properties is expected to be absorbed efficiently. Accordingly, designing a sustained action preparation with an inhalant may become a widely applicable useful technique.

Fourthly, it is a matter of course that an inhalant as well as other forms of medicaments is desired to be used simply. Especially, an inhalant is desired to be easily and readily used at the time of a paroxysm of asthma, etc.

Next, in view of the physicochemical aspect of an inhalant, firstly, fine particles constituting preparations are desirably uniform regardless of whether the preparations are in solution or in powder. Requirements of the particle uniformity are not only a matter of course from the standpoint of quality standards but also a necessity for surely realizing delivery and deposition of the fine particles within an airway to obtain the efficacy of the preparations. Secondly, preparations are desirably stable. Particularly in the case of medicaments used for chronic diseases such as asthma and bronchitis, preparations capable of being preserved at room temperature are desired. Thirdly, preparations should be capable of being industrially produced in good yields. The preparations should therefore be produced by a method enabling the industrial production mentioned above possible.

In view of desired properties of inhalants as described above, it is understood from examination of the forms of the above-mentioned conventional inhalants that these inhalants do not necessarily satisfy all the desired properties.

Firstly, droplets having a particle size of 0.5 to 10 μm can be efficiently generated from solutions if a nebulizer of suitable performance is selected. However, a nebulizer is required to generate mist, and it can be used neither simply nor conveniently nor portably. Solutions are difficult to retain at target sites because they are aqueous, although solutions cause no problem of irritation if the additives are selected appropriately. In addition, a liposome preparation has been proposed as means for improving the retaining properties in a solution state at target sites (see Japanese Unexamined Patent Publication No. 58-128318). However, liposomes are in general unstable, and are difficult to be preserved at ordinary temperature, for example, at room temperature over a long period. It is understood from the aforementioned description that the conventional solutions are not always satisfactory.

Secondly, an aerosol utilizing fluorohydrocarbon can efficiently generate fine particles having a particle size of 0.5 to 10 μm when medicament particles to be dispersed in the fluorohydrocarbon are powdered finely. Use of an aerosol is simple if a metered dose inhaler is used, and the problem of irritation scarcely occurs. Problems as to uniformity, safety and productivity seldom occur when an aerosol is used. However, control of the use of fluorohydrocarbon is demanded because of the problem of global environmental pollution. As described above, an aerosol agent utilizing fluorohydrocarbon is not always satisfactory and replacement of an aerosol agent is strongly demanded in view of environmental problems.

Thirdly, although inhalants prepared as powders have heretofore been relatively insufficiently developed, much attention has quickly been drawn thereto because of the necessity of developing a simple administration method which is free of the fluorohydrocarbon problems mentioned above and which replaces solutions. There are the following three types of conventional powders:

(1) A well-mixed powder comprising ultrafine medicament particles and excipient particles selected from lactose, etc., and having a particle size larger than that of the medicament particles, the excipient being deposited at an oral cavity, pharynx or larynx and only the ultrafine medicament particles being delivered to and deposited at a lower airway such as a trachea and bronchi when the particle mixture is administered to within an airway from a suitable container;

(2) A powder composed of medicament particles having a relatively large particle size prepared by mildly granulating ultrafine medicament particles, the granulated powder being disintegrated into the constituent ultrafine medicament particles during its flight when administered to an airway from a suitable container, the thus formed medicament ultrafine particles being delivered to and deposited at a lower airway such as a trachea and bronchi; and (3) A powder consisting only of ultrafine medicament particles, and being delivered to and deposited at a lower airway such as a trachea and bronchi when administered to an airway from a suitable container.

These three types of powders still have unsolved problems as described below.

With regard to powders in (1) and (3), only medicament particles are deposited at target sites, and retention and sustained release thereof at the sites are difficult to ensure.

Retention and sustained medicament release at target sites of a powder in (2) is difficult to ensure, the situation being similar to that of powder in (1). Moreover, ultrafine medicament particles themselves cannot be mildly granulated in some cases due to the physical properties of the medicament itself. An amount of disintegration into the constituent ultrafine particles may sometimes differ, and as a result a delivered amount and a deposited amount at target sites may vary.

Accordingly, there is desired realization of a powder inhalant which exhibits good delivery to and good deposition at a lower airway such as a trachea and bronchi, and which is excellent in retention and medicament sustained release as deposition sites.

Microcapsules prepared from a polylactic acid, a biodegradable polymer, for such a powder inhalant have been proposed (see Japanese Unexamined Patent Publication No. 3-17014). Although sustained medicament release from the microcapsules can be expected in this method, adhesion to and retention at a lower airway mucosa of the microcapsules themselves are most difficult to ensure. Since formation of the ultrafine particles is not easy and forming the particles having a particle size of 0.5 to 10 μm is very difficult, the productivity of the inhalant is low. Furthermore, the inhalant has a disadvantage that removal of the organic solvent used in microencapsulation of the inhalant is not easy.

Accordingly, there is desired realization of a powder inhalant which exhibits good delivery to and good deposition at a lower airway such as a trachea and bronchi, which is excellent in retention and medicament sustained release at deposition sites and which is also excellent in all of such properties as productivity, stability, safety and uniformity.

In addition, with regard to a pharmaceutical composition comprising a cellulose lower alkyl ether and a medicament, the present inventors have disclosed a sustained action preparation for a nasal cavity in Japanese Examined Patent Publication No. 60-7965. The ultrafine particle powder for inhalation comprising a specific cellulose lower alkyl ether and a medicament of the present invention and a preparation containing the ultrafine particle powder should be clearly distinguished from the preparation disclosed in the above-mentioned patent publication by the following respects:

(1) The invention of the patent publication relates to a preparation for a nasal cavity, whereas the present invention relates to a preparation for inhalation capable of being delivered principally to a lower airway. The particle size distributions of both preparations can be definitely distinguished from each other.

(2) There is no disclosure in the patent publication which suggests that the composition of the invention may further be pulverized to give ultrafine particles for use in inhalation.

(3) The ultrafine particles for inhalation of the present invention which are capable of being delivered principally to a lower airway differ from the composition for a nasal cavity disclosed in the above-mentioned patent publication in that the ultrafine particles cannot be produced by the method wherein a cellulose lower alkyl ether and a medicament are mixed to give a composition. A cellulose lower alkyl ether prior to mixing cannot even be ground to give particles having a particle size suitable for an inhalant. That is, medicament particles of an inhalant generally have a particle size distribution of approximately 0.5 to 10 μm, and they are usually prepared by grinding using a jet mill, and the like. However, a cellulose lower alkyl ether in fine particles having a particle size less than 10 μm cannot be obtained in a high yield at least by dry grinding. Even when ultrafine particles of a cellulose lower alkyl ether can be obtained, it is very difficult to obtain appropriately agglomerated fine particles which behave uniformly, by mixing the ultrafine particles with medicament ultrafine particles. The ultrafine particles for inhalation of the present invention can be produced only by spray drying.

(4) Furthermore, Japanese Examined Patent Publication No. 60-7965 discloses the use of cellulose lower alkyl ethers as bases constituting powder preparations, together with a medicament for a powder preparation for administration to nasal cavity mucosa having a particle size of 20–250 μm for 90% by weight or more of the particles. Examples of such cellulose lower alkyl ethers are methyl cellulose, hydroxyethyl cellulose, hydroxypropyl cellulose, hydroxypropylmethyl cellulose, sodium carboxymethyl hydroxyethyl cellulose, sodium carboxymethyl cellulose. Among these, it is disclosed that methyl cellulose, hydroxypropyl cellulose, hydroxypropyl methyl cellulose are preferable in view of smell and irritation. On the other hand, according to the present invention, hydroxypropyl cellulose and hydroxypropyl methyl cellulose are selected as a component constituting a powder preparation having a particle size of 0.5–10 μm for 80% by weight or more thereof. However, the reasons for the selection thereof is a completely different technical idea from those of the above-mentioned powder preparation for nasal cavity mucosa. Namely, as mentioned above, the most important property for the inhalant is a particle size thereof. Regarding this point, it is surprisingly found from the following two experiments that the hydroxypropyl cellulose and hydroxypropyl methyl cellulose according to the present invention are different from the other cellulose lower alkyl ethers (the details will be further described later as Reference Experiments).

Experiment 1: Stability of Particle Size During Storage of Fine Particle For Inhalant According to the present method, powder (A) comprising beclometasone dipropionate and hydroxypropyl cellulose and having a particle size of 0.5–10 μm for 80% by weight or more thereof, powder (B) comprising beclometasone dipropionate and hydroxypropyl methyl cellulose and having the same particle size as mentioned above, powder (C) comprising beclometasone dipropionate and methyl cellulose and having the same particle size as mentioned above, powder (D) comprising beclometasone dipropionate and hydroxyethyl cellulose and having the same particle size as mentioned above, powder (E) comprising beclometasone dipropionate and sodium carboxymethyl hydroxyethyl cellulose and having the same particle size as mentioned above and powder (F) comprising beclometasone dipropionate and sodium carboxymethyl cellulose and having the same particle size were prepared by a spray drying method.

Contrary to the above, according to the method disclosed in Japanese Examined Patent Publication No. 60-7965, mixed powder (G) of beclometasone dipropionate and hydroxypropyl cellulose having a particle size of 20–250 μm for 90% by weight or more thereof, mixed powder (H) of beclometasone dipropionate and hydroxypropyl methyl cellulose having the same particle size as mentioned above, mixed powder (I) of beclometasone dipropionate and methyl cellulose having the same particle size as mentioned above, mixed powder (J) of beclometasone dipropionate and hydroxyethyl cellulose having the same particle size as mentioned above, mixed powder (K) of beclometasone dipropionate and sodium carboxymethyl hydroxyethyl cellulose having the same particle size as mentioned above and mixed powder (L) of beclometasone dipropionate and sodium carboxymethyl cellulose having the same particle size were prepared by a mechanical mixing method.

Furthermore, powder (M) to powder (R) having the combination corresponding to that of the above-mentioned powder (G) to powder (L), respectively, were prepared by a spray drying method in such a manner that the particle size of 90% by weight or more was within the same range of 20 to 250 μm.

The above-mentioned powders (A)–(R) were humidified at 25° C./50% R.H. for 48 hours, followed by measuring the particle sizes by a particle size distribution measuring apparatus of a laser diffraction type. Therefore, the powders were allowed to stand at 25° C./65% R.H. for 7 days, followed by measuring the particle sizes by the same method. As a result, in the case of the powders (G)–(L) and (M)–(R) having the necessary particle size distribution for preparation for nasal cavity administration, no particle size changes after storage were observed, irrespective of kinds of the cellulose lower alkyl ethers. Contrary to this, in the case of the powders (A)–(F) having the necessary particle size distribution for an inhalant, the powders (A) and (B) using hydroxypropyl cellulose and hydroxypropyl methyl cellulose did not exhibit the particle size change after storage. However, in the cases of the other powders using methyl cellulose (C), hydroxyethyl cellulose (D), sodium carboxymethyl hydroxyethyl cellulose (E), and sodium carboxymethyl cellulose (F), the presence of a large size particle was observed, which was presumed by the formation of agglomerated mass of the original particles.

Experiment 2: Depositionability of Fine Particle for Inhalation within Lung

The powders (A)–(F) for an inhalant used in the above-mentioned Experiment 1 were examined, regarding the depositionability thereof within a lung under a humidified condition (i.e., 37° C./98%), by a cascade impactor. As a result, the powder (A) containing hydroxypropyl cellulose and the powder (B) containing hydroxypropyl methyl cellulose according to the present invention exhibited such an average aerodynamic radius that, when these powders are actually administered to human beings, it is estimated that a sufficient amount thereof is deposited on a trachea, a primary bronchus and peripheral lung portions therefrom. However, the other powders (C) to (F) containing the other cellulose lower alkyl ethers exhibited such an average aerodynamic radius that it is estimated that these powders are deposited on a larynx. Thus, it is estimated that the powders are not possible to be deposited on the targeted portions, i.e., a trachea, a primary bronchus and peripheral lung portions therefrom.

Although it is not clear why the remarkable difference between hydroxypropyl cellulose, hydroxypropyl methyl cellulose and the other cellulose lower alkyl ethers occurs, it is estimated that this difference is related to the hygroscopicity (equilibrium moisture) of the cellulose lower alkyl ethers. It is known that the hygroscopicity of hydroxypropyl cellulose, hydroxypropyl methyl cellulose is lower than that of methyl cellulose, hydroxyethyl cellulose, sodium carboxymethyl cellulose, sodium carboxymethyl hydroxyethyl cellulose. Nevertheless, it is not expected by those skilled in the art that the above-mentioned difference in the hygroscopicity causes the above-mentioned remarkable difference between the particle size required for the inhalant and the particle size required for the preparation for administration to nasal cavity (in which no substantial differences are observed), regarding the agglomeration or growth of the particles, shown in the above-mentioned Experiments.

As is clear from the above two Experiments, the technical idea according to the present invention finding the use of hydroxypropyl cellulose and hydroxypropylmethyl cellulose among the cellulose lower alkyl ethers and the technical idea selecting, as a preferable one, hydroxypropyl cellulose, hydroxypropyl methyl cellulose, methyl cellulose among the same cellulose lower alkyl ethers are completely different. Furthermore, the technical idea according to the selection of the present invention is an essential matter for the inhalant technique and exhibit the novelty and inventive step of the present invention.

From the illustration described above, it will be understood that the ultrafine particle powder for inhalation of the present invention is entirely different from the composition for a nasal cavity disclosed by Japanese Examined Patent Publication No. 60-7965.

On the other hand, it has already been known that a pharmaceutical composition comprising a cellulose lower alkyl ether and a medicament is produced by spray drying. For example, medicament particles are coated with hydroxypropyl cellulose by spray drying, whereby hydroxypropyl cellulose masks the taste of the medicament itself and controls elution thereof. M. Vidgren et el. have reported that fine particles having a particle size of approximately 3 to 10 $\mu$m and comprising cromoglycate disodium or beclometasone dipropionate, and polyacrylic acid and/or sodium carboxymethyl cellulose are obtained by spray drying, and that the resultant fine particles exhibit sustained releasing properties and mucosa-adhesivity (Drug Development and Industrial Pharmacy, 18 (5), 581–597, 1992, 6th International Conference on Pharmaceutical Technology, Paris Jun. 2–4, 1992). However, production, by spry drying, of ultrafine particles comprising a specific cellulose lower alkyl ether and a medicament and having the particle distribution of the present invention has never been disclosed, and the use of the ultrafine particles of the present invention as an inhalant capable of being delivered principally to a lower airway has not even been suggested.

DISCLOSURE OF INVENTION

In accordance with the present invention, there is provided an ultrafine particle powder for inhalation comprising hydroxypropyl cellulose, and/or hydroxypropyl methyl cellulose, and a medicament, at least 80% of the powder having a particle size of 0.5 to 10 $\mu$m.

It will be understood from the above description that the ultrafine particle powder for inhalation of the present inventors comprising hydroxypropyl cellulose and/or hydroxypropyl methyl cellulose and a medicament and containing particles having a particle size of 0.5 to 10 $\mu$m in an amount of at least 80% is a novel technical conception which cannot be obtained even from the analogy to the conventional technical idea.

As a result of intensively carrying out research on the problems mentioned above, the present inventors have discovered that when an ultrafine particle powder comprising hydroxypropyl cellulose and/or hydroxypropyl methyl cellulose, and a medicament, at least 80% of the powder having a particle size of 0.5 to 10 $\mu$m, is used as an inhalant, the powder becomes an inhalant exhibiting good delivery to and good deposition at a lower airway such as a trachea and bronchi, being excellent in retaining properties and sustained releasing properties of the medicament at deposition sites, and having excellent properties such as efficient productivity, stability, safety and uniformity. The present invention has been achieved on the basis of the discovery.

Furthermore, in accordance with the present invention, there is provide a method for the production, by spray drying, of an ultrafine particle powder for inhalation comprising hydroxypropyl cellulose and/or hydroxypropyl methyl cellulose and a medicament, at least 80% of the powder having a particle size of 0.5 to 10 $\mu$m.

Furthermore, in accordance with the present invention, there is provide a powder preparation for inhalation comprising such an ultrafine particle powder for inhalation. Since such an ultrafine particle powder for inhalation of the present invention has a particle size in a specific numerical range, it is capable of being delivered principally to a lower airway.

BRIEF EXPLANATION OF DRAWINGS

The present invention will now be further explained with reference to the attached drawings, wherein.

BEST MODE FOR CARRYING OUT THE INVENTION

According to the present invention, among cellulose lower alkyl ethers, hydroxypropyl cellulose and/or hydroxypropyl methyl cellulose are used as an inhalant. This is because, since the hydroxypropyl cellulose and/or hydroxypropyl methyl cellulose have a lower hygroscopicity, when compared with the other cellulose lower alkyl ethers, the stability of particle distribution and the inhalation feasibility to an airway are excellent. Furthermore, since hydroxypropyl cellulose and/or hydroxypropylmethyl cellulose are water-soluble, they absorb water on the mucosa after deposited on an airway and afford moderate adhesive properties and fluidity to thereby effect sustain release of the medicament and, thereafter, they are dissolved into a liquid layer covering the airway and removed therefrom by transportation through the cilium for mucilage. In addition, since hydroxypropyl cellulose is dissolved in a lower alcohol and since hydroxypropyl methyl cellulose is dissolved in a mixture of ethanol and dichloromethane, a mixture thereof with a much wider variety of medicaments such as steroids which are insoluble in water can be formulated. For these reasons, in the present invention, hydroxypropyl cellulose and hydroxypropyl methyl cellulose can be used as a preferable base for sustained release of medicaments for inhalation.

Examples of the medicament used in the present invention include medicaments used for local treatment of thoracopathy such as asthma; medicaments not suited to oral administration due to instability in a digestive tract, such as peptide proteins and low molecular weight organic synthetic compounds; medicaments which are recognized to exhibit improvement in quick efficacy and absorption when administered by inhalation compared with oral administration; and vaccines intended to induce mucosa type local immunity.

Typical examples of the medicament include steroids such as beclometasone dipropionate, triamcinolone acetonide and flunisolide; antiallergics such as cromoglycate disodium; elastase inhibitors such as SLPI; chemotherapy medicaments for infective diseases such as gentamycin, kanamycin, carbenicillin, amphotericin B, ribavirin and pentamidine; antitussives such as codeine phosphate; bronchodilators such as salbutamol hemisulfate; antineoplastic medicaments such as 5-fluorouracil; physiologically active peptide proteins such as insulin, calcitonin and SLPI; anti-migraines such as ergotamine tartrate; vaccines (the local immunity on the mucosa obtained therewith being efficacious in preventing infection and pathopoiesis of viruses such as an influenza virus); and medicaments for circulatory organs.

These medicaments may be used singly, or as a mixture of two or more thereof unless the mixture is incompatible.

Of these medicaments mentioned above, steroids such as beclometasone dipropionate and antiallergics such as cromoglicate disodium particularly exhibit improved efficacy when used as a powder preparation for inhalation containing the ultrafine particle powder of the invention.

The ultrafine particle powder for inhalation of the invention comprises the cellulose lower alkyl ether in an amount of preferably 5.0 to 99.8% by weight, more preferably 20.0 to 99.0% by weight per particle thereof.

The ultrafine particle powder for inhalation of the invention comprises a medicament in an amount of preferably 0.2 to 95.0% by weight, more preferably 1.0 to 80.0% by weight per particle thereof.

The particle size of the ultrafine particle powder for inhalation of the invention is such that at least 80% of the powder has a particle size of 0.5 to 10 $\mu$m.

The ultrafine particle powder for inhalation of the invention comprising the cellulose lower alkyl ethers and a medicament, at least 80% by weight of the powder having a particle size of 0.5 to 10 $\mu$m, is produced by spray drying.

The spray drying according to the present invention refers to a method wherein the specific cellulose lower alkyl ether and a medicament of the invention are dissolved in a solvent, or the medicament which is ultrafinely ground is suspended in a solution containing the cellulose lower alkyl ether, and the resultant solution or suspension is spray dried by a conventional method. For example, the ultrafine particle powder for inhalation of the invention is obtained by the following procedures: the cellulose lower alkyl ether according to the present invention is dissolved in a solvent such as water or an alcohol capable of dissolving the alkyl ether, and a medicament is further dissolved or ultrafinely ground and suspended therein; and the resultant sample solution or suspension is spray dried by a nozzle type apparatus. The ultrafine particle powder for inhalation of the invention comprising a cellulose lower alkyl ether and a medicament, and having the intended particle size distribution of 0.5 to 10 $\mu$m can be obtained in a high yield by adjusting a spraying pressure of the spray drier, a nozzle diameter and a concentration of the sample solution. In the case where the resultant powder contains a large proportion of particles having a particle size exceeding 10 $\mu$m, it is necessary to remove them by screening.

The ultrafine particle powder for inhalation of the present invention comprising the cellulose lower alkyl ether and a medicament is required to be adjusted in such a manner that approximately at least 80% of the powder has a particle size distribution of 0.5 to 10 $\mu$m, whereby the ultrafine particle powder is suited to be delivered to and deposited in a lower airway of a human. The ultrafine particle powder is then efficiently formed into mist by inspired gas or a propellant such as gas, and is administered by inhalation.

The ultrafine particle powder for inhalation of the invention is required to have pharmaceutically acceptable macroscopic mixing uniformity. That is, any portion of the powder is always required to have a uniform medicament concentration. Moreover, the ultrafine particle powder for inhalation of the invention is required to be in a microscopically uniform mixed state which is pharmaceutically acceptable, and as a result the percentage composition of a fraction thereof delivered to and deposited in a respiratory apparatus of a human should agree with the entire percentage composition thereof. Although the ultrafine particle powder for inhalation of the present invention should be microscopically in a uniform mixed state, the medicament may be completely mixed with a cellulose lower alkyl ether, in an amorphous state, or it may be dispersed therein, in a microcrystalline state, or it may be in an intermediate state between the above-mentioned two states.

Although the ultrafine particle powder for inhalation of the present invention comprises the specific cellulose lower alkyl ether and a medicament, its properties may be improved, if necessary, by adding in advance to a sample solution to be spray dried a lubricant such as magnesium stearate, etc., a surfactant such as soybean lecithin, an antistatic agent, a stabilizer, an odor-changing agent, and the like.

The ultrafine particle powder for inhalation of the present invention may be used as a powder preparation for inhalation alone or in a mixture with other additives such as a carrier having a dispersing and/or diluting function or in a pneumatic dispersion with a propellant such as gas.

In the case where the ultrafine particle powder for inhalation of the present invention is used alone as a powder preparation for inhalation, the particle powder may be administered by a system wherein one dose thereof is filled in a capsule, and the contents are taken out at the time of the use thereof, or by a multi-dose system wherein one dose thereof is separately poured from a storage tank at the time of the use thereof. In any of the two systems, the ultrafine particle powder is administered by a powder inhaler which pneumatically disperses it with a suction gas.

A carrier such as lactose, dextran, mannitol and maltose may be used for the ultrafine particle powder of the present invention in order to prevent adhesion thereof to capsules and inhalers and agglomeration thereof (dispersion function), and inhibit an increase in weight deviation thereof in the process of filling a very small amount thereof in capsules, etc. (diluting function). The carrier particles have a particle size of preferably 30 to 150 $\mu$m, and the proportion thereof to be mixed with the ultrafine particle powder is determined by a necessary amount of the medicament. Mixing the ultrafine particle powder and the carrier can be carried out by a mixer of container-rotary type or mechanical stirring type. Moreover, a lubricant, etc., may also be mixed with the ultrafine particle powder in order to improve the dispersibility and container-adhesivity thereof. The powder preparation for inhalation thus obtained is administered using a powder inhaler which pneumatically disperses the preparation through a suction air by a system wherein one dose thereof is separately poured in a capsule or by a system wherein one dose thereof is separately poured at the time of use thereof.

The ultrafine particle powder for inhalation of the invention may also be pneumatically dispersed by mixing the powder with a suitable amount of a surfactant such as soybean lecithin and sorbitan trioleate, and suspending the resultant mixture in a spraying agent for aerosol such as fluorohydrocarbon.

[Industrial Applicability]

Thus, the present invention provides a powder inhalant exhibiting good delivery to a lower airway such as a trachea and bronchi, and excellent retention and sustained releasing properties of the medicament at deposition sites, and being excellent in productivity, stability, safety and uniformity. Accordingly, the present invention is very significant.

EXAMPLES

The present invention will now be illustrated in detail below with reference to Examples, but The examples are described in order to illustrate the present invention, without being a limitation thereof.

Example 1

In this Example, an ultrafine particle powder mixture of hydroxypropyl cellulose (HPC) and beclometasone dipropionate (BDP) was prepared by spray drying of the present invention, and the properties thereof were evaluated.

Hydroxypropyl cellulose and beclometasone dipropionate were dissolved in ethanol so that the percentage composition of beclometasone dipropionate and the concentration of the total solid substances (solutes) became approximately up to 80% and approximately 2 to 5 (wt./vol.)%, respectively. The resultant solution was spray dried using a spray dryer of two-fluid nozzle spray type (trade name of GS 31, manufactured by Yamato Scientific Co., Ltd.) to give a powder in a yield of approximately 45 to 80%. The percentage composition of the powder well corresponded to that of the charged value. The uniformity of the powder was examined by random sampling thereof (n=30), and the CV value thus obtained was 3.1%, which value proved that the powder was a fairly uniform mixture. It was confirmed from the results of electron microscopic observation thereof that the particle size was well in correspondence with that obtained by laser diffraction measurement, and that the shape of the particles was close to a sphere when the content of beclometasone dipropionate was high and became creased and withered as the content fell. The particle size distribution of a powder with a BDP content of 20% selected as a typical example was measured using a particle size distribution measuring apparatus of laser diffraction type (trade name of JEOL/SYMPATEC, manufactured by Heros & Rodos), and the results are shown in FIG. 1. It is evident from FIG. 1 that at least 80% of the powder exhibited a particle size distribution of 0.5 to 10 μm.

X-ray diffraction analysis of the powder was carried out, and the results are shown in FIG. 2. It was found from FIG. 2(A) that BDP was amorphous in the powder mixture, and that a uniform powder was obtained. X-ray diffraction analysis of a powder prepared by mixing BDP and HPC using a mortar was carried out for reference, and the results are shown in FIG. 2(B). It was found from FIG. 2(B) that BDP was in a crystalline state.

Example 2

In this Example, an ultrafine particle powder mixture of hydroxypropyl cellulose and disodium cromoglycate was prepared by spray drying, and the properties thereof were evaluated.

A solution prepared by dissolving hydroxypropyl cellulose and cromoglycate disodium in water was spray dried in the same manner as in Example 1. Approximately 80% of the powder mixture thus obtained had a particle size distribution of 0.5 to 10 μm.

Example 3

In this Example, an ultrafine particle powder mixture of hydroxypropyl cellulose and beclometasone dipropionate was prepared by a spray drying method, and the properties thereof were evaluated.

Hydroxypropyl methyl cellulose and beclometasone dipropionate were dissolved in 1/1 (volume ratio) mixture of ethanol and dichloromethane so that the concentration of beclometasone dipropionate became approximately up to 80% and that the concentration of the total solid substance (solutes) became approximately 0.5–2 (wt./vol.)%, followed by spray drying.

The powder was recovered at approximately 50 to 70% the composition ratio well corresponded to the charged value and the powder was substantially uniformly mixed. The particle size distribution, determined by a particle size distribution measuring apparatus of a laser diffraction type, was 0.5–10 μm for 80% or more of the powder.

Example 4

In this Example, the determination of clinical administration method of the mixed ultrafine particle powder of hydroxypropyl cellulose and beclometasone dipropionate, produced by a spray drying, and the effective amount of administration (the amount of deposition at a diseased portion of airway were evaluated).

Hydroxypropyl cellulose and beclometasone dipropionate were dissolved in ethanol so that the percentage composition of beclometasone dipropionate and the concentration of the total solid substances (solutes) became approximately up to 20% and approximately 1.25 (wt./vol.)%, respectively. The resultant solution was spray dried to obtain the mixed ultrafine particle powder having an average size of 1.8 μm (50% under cumulative size) and a geometric standard deviation of 2.3. The resultant powder was uniformly mixed with 9 times by weight of lactose for an inhalant (Pharmatose 325M available from DMV Corp.) by a V type mixer to obtain the powder preparation for inhalation.

The resultant powder preparation for inhalation was filled into #3 gelatin capsules in an amount of 5 mg each (containing 100 μg of beclometasone dipropionate) and charged, through a suction air, into an inhaler which generates the powder preparation through a suction air. This inhaler is structured such that a hole is opened on each of the top portions of the capsule by a needle before the inhalation and a powder preparation contained therein is effectively discharged and atomized during inhalation, while providing an appropriate vibration to the capsule. The inhaler was mounted on a cascade impactor (an Andersen sampler) via an induction port, which is a model of an upper airway. The atomizing evaluation test of the preparation was carried out with an amount of suction air of 56.6 liter/min. As a result, the deposition to the lower airway was 12% and the deposition from the oral cavity to the upper airway was 44%, which are equivalent to the effective doses of a commercially available inhalant.

Example 5

This Example evaluates in vivo the particle deposition distribution and retention of a medicament in an airway, using guinea pigs, of the mixed ultrafine powder of hydroxypropyl cellulose and a fluorescent dye, fluorescein, prepared by spray drying.

Hydroxypropyl cellulose and fluorescein were dissolved in ethanol such that the composition ratio of fluorescein was 20% and the total concentration of solids (elute) was 1.25 (wt./vol.)%, followed by spray drying and uniformly mixing to obtain the ultrafine powder.

Figure 1:
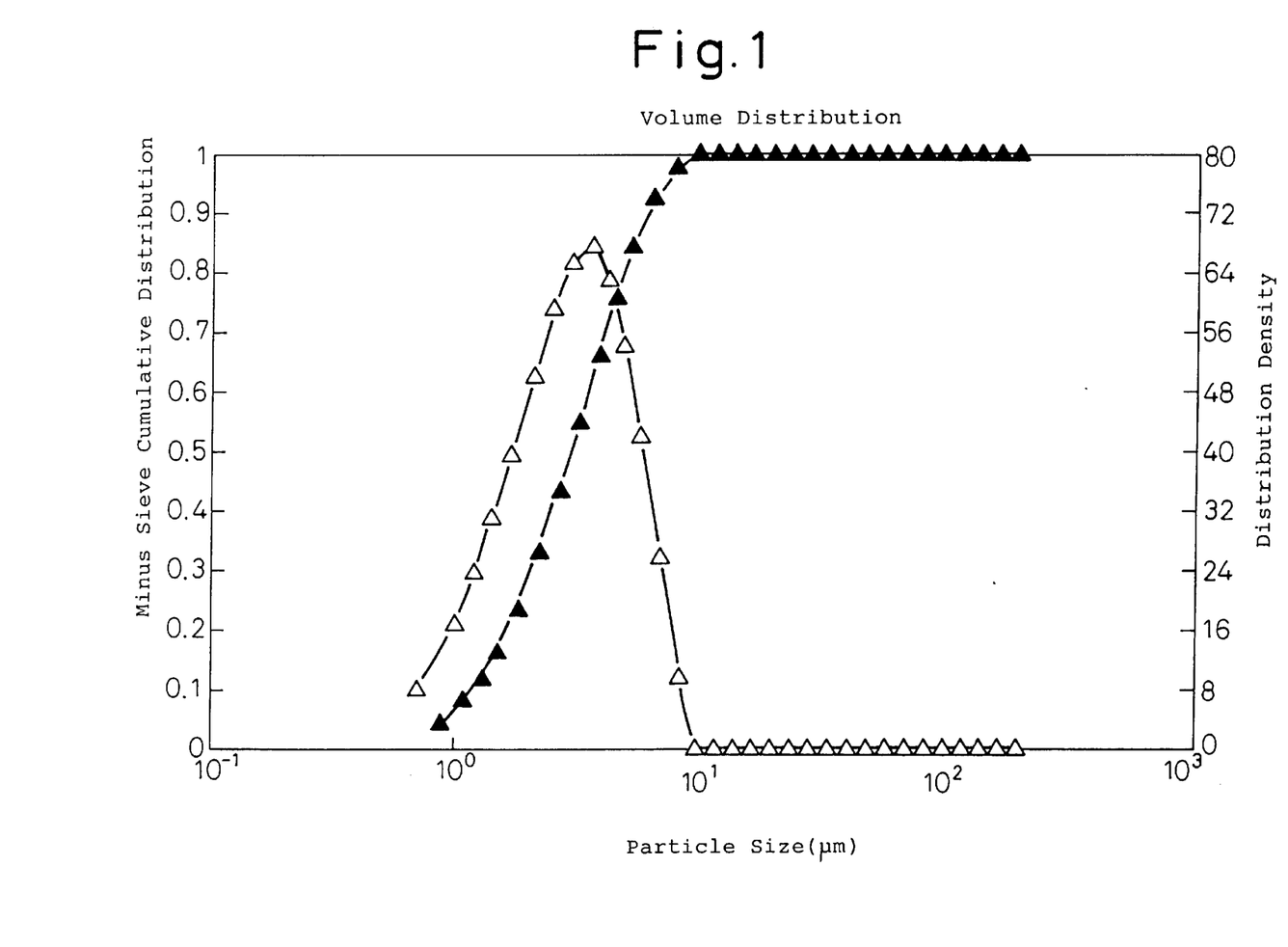
FIG. 1 shows a particle size distribution of an ultrafine particle powder for inhalation of the present invention (BDP:HPC=1:4) in Example 1. In the Figure, the marks Δ—Δ show a distribution density thereof, and the marks ▲—▲ show a minus sieve cumulative distribution thereof.
Figure 2A:
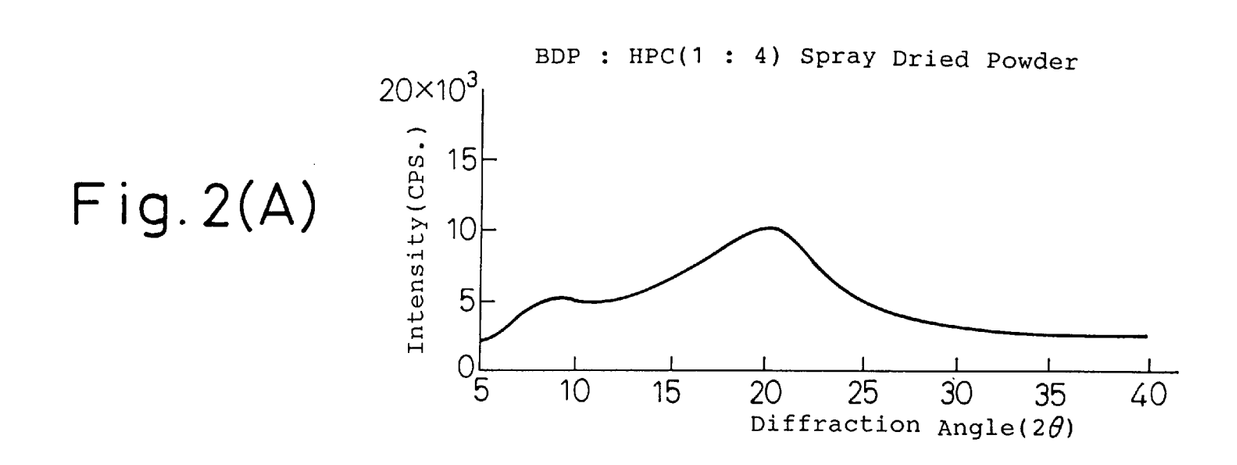
FIG. 2(A) shows results of X-ray diffraction analysis of the ultrafine particle powder for inhalation (BDP:HPC=1:4) obtained by the method of the present invention in Example 1.
Figure 2B:
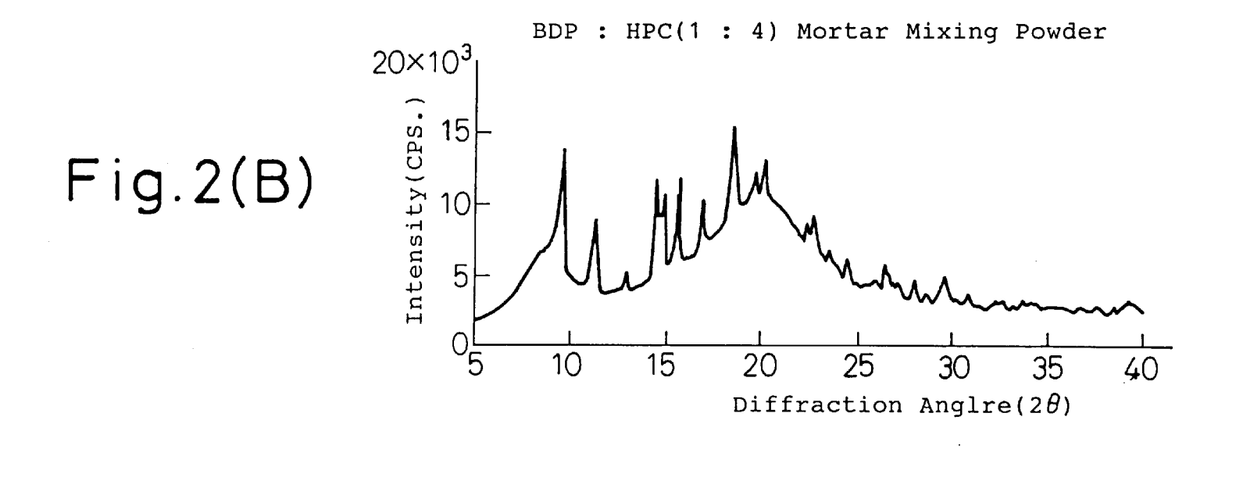
FIG. 2(B) shows results of X-ray diffraction analysis of a powder (BDP:HPC=1:4) prepared by mixing, using a mortar.
Figure 3:
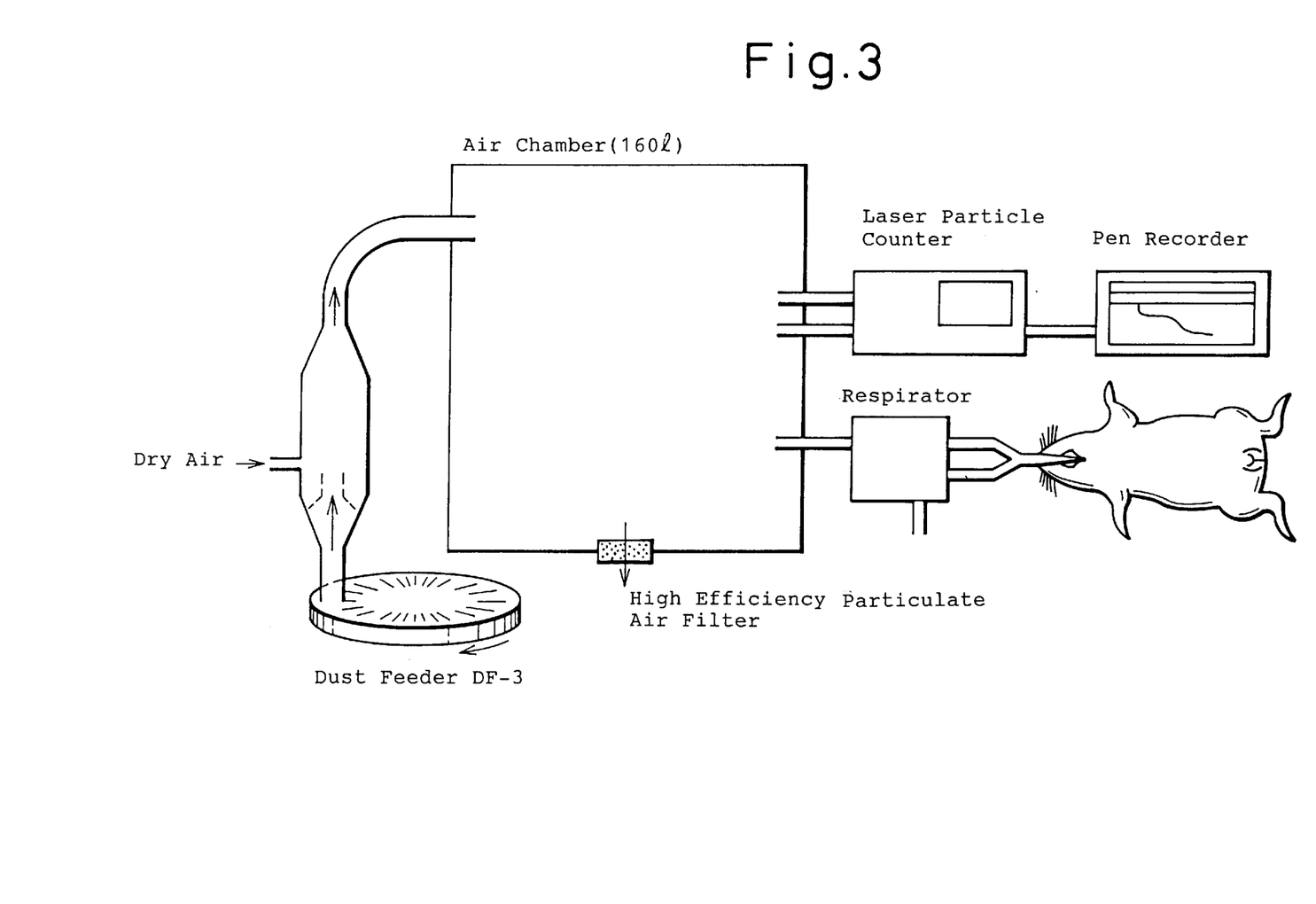
FIG. 3 is a drawing showing an evaluation method of an ultrafine particle powder for inhalation according to the present invention using guinea pigs in Example 5.

The resultant mixed ultrafine powder was steadily converted to aerosol in an apparatus comprising a dust feeder DF-3 (Shibata Kagaku) connected to a 160 liter air chamber. The aerosol concentration and the aerodynamic particle size distribution were determined by connecting a laser particle counter and a cascade impactor to the air chamber (FIG. 3). The aerosol concentration was stable with the lapse of time and the average aerodynamical size was 1.8 μm and geometric standard deviation was 2.1.

Figure 4:
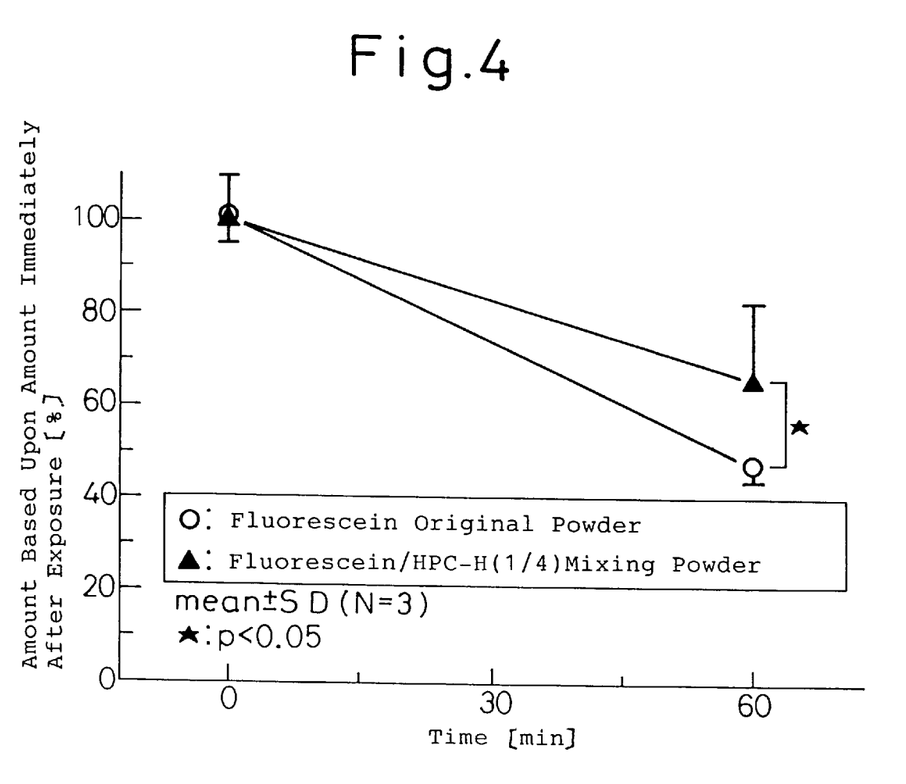
FIG. 4 shows a degree of retention, in an airway and lung, of mixed ultrafine powder of hydroxypropyl cellulose and fluorescein in Example 5.
Figure 5:
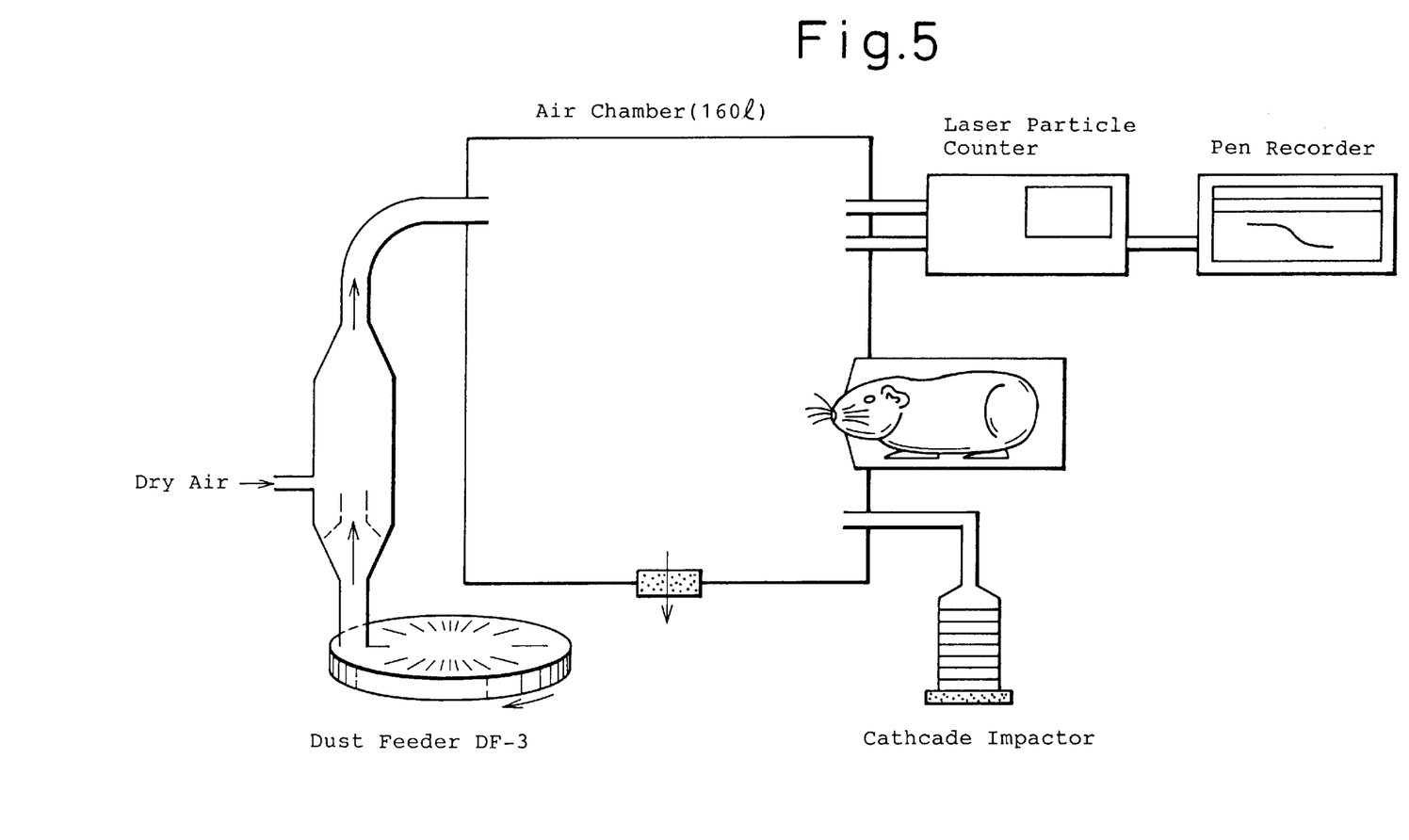
FIG. 5 is a drawing showing a method for evaluating airway clearance in vivo of an ultrafine powder of $^{14}$C labeled hydroxypropyl cellulose and hydroxypropyl methyl cellulose in Example 6.

The guinea pig (Hartley's, Male: 6 weeks old) was provided with a tracheal cannula under anesthetization and was exposed to the powder aerosol by a respirator piped from the air chamber at a ventilation amount of 2.5 ml per 1 time and a ventilation frequency of 80 times/min (FIG. 3). The distribution of fluorescein deposited in an airway immediately after exposure was 40% from trachea to secondary bronchus and 60% at the peripheral airways and lung from the secondary bronchus. Thus, good particle arrivality was exhibited. Furthermore, as shown in FIG. 4, the retention amounts of fluorescein at the airway and lung one hour after exposure are significantly higher than those of the control, i.e., fluorescein crystalline fine power having the same aerodynamic particle distribution and airway deposition distribution as those of the above-mentioned mixed ultrafine powder. Thus, the retentionability was observed.

Example 6

This Example evaluates the in vivo airway clearance of ultrafine powder of $^{14}C$ labeled hydroxypropyl cellulose and hydroxypropyl methyl cellulose prepared by spray drying.

The $^{14}C$ labeled hydroxypropyl cellulose and hydroxypropyl methyl cellulose were synthesized with $^{14}C$-propylene oxide as an etherification agent. The $^{14}C$-hydroxypropyl cellulose was dissolved in an ethanol and the $^{14}C$-hydroxypropyl methyl cellulose was dissolved in 1/1 (vol. ratio) mixture of ethanol/dichloromethane such that the concentrations became 1.25 (wt./vol.)% and 1.00 (wt./vol.)%, followed by spray drying, to obtain the ultrafine powder.

The resultant $^{14}C$ labeled ultrafine powder as inhalation administered repeatedly for 7 days to Hartley's male guinea pig (6 weeks age) at a dosage of 200 μg/kg/day. After the administration, the retention amount thereof in lung and the discharge amount in the feces for 96 hours were determined, no radioactive activity was found in lung and the discharge of 93% or more of the administered amount of the radioactivity was confirmed in the feces. As a result, it is considered that the hydroxypropyl cellulose and hydroxypropyl methyl cellulose deposited on the airway and lung administered by inhalation were eliminated through mucociliary clearance and, without causing the absorption thereof at a lung and the migration to body fluid, was swallowed.

Example 7

(Reference Experiment 1: showing stability in particle size of Examples 1 and 7)

Fine powders comprising the following cellulose lower alkyl ethers and beclometasone dipropionate were prepared by a spray dryer (Yamato Kagaku: GS-31) in the similar manner as the fine powder comprising hydroxypropyl cellulose and beclometasone dipropionate, obtained in Example 1.

| No. | Cellulose lower alkyl ethers |
| --- | --- |
| Example 1 | Hydroxypropyl cellulose |
| Example 7 | Hydroxypropyl methyl cellulose |
| Control Example 1 | Methyl cellulose |
| Control Example 2 | Hydroxyethyl cellulose |
| Control Example 3 | Sodium carboxymethyl cellulose |
| Control Example 4 | Sodium carboxymethyl hydroxy ethyl cellulose |

In Example 7, hydroxypropyl methyl cellulose and beclometasone propionate were dissolved in a mixture of ethanol/dichloromethane and the resultant solution was spray dried in the spray dryer to produce the powder. On the other hand, in Control Examples 1–4, the ultrafinely divided beclometasone dipropionate having a size of about 0.5 μm was dispersed in an aqueous solution of cellulose lower alkyl ethers and the resultant dispersion was spray dried in the spray dryer to obtain the fine powder. The powders of Example 1, Example 7 and Control Examples 1–4 were stored under the conditions of 25° C./50% R.H. for 48 hours and then the particle size distribution was measured by a laser diffraction type particle size distribution measuring apparatus. As a result, it was confirmed that 80% by weight or more of the particles were within the range of 0.5 to 10 μm. After storing these powders under the conditions of 25° C./65% R.H. for 7 days, the particle size distributions were measured. As a result, although no substantial changes were observed in Examples 1 and 7, the particles within the range of from 0.5 to 10 μm were decreased to 50% by weight or less and the amount of the particles having a size of 10–100 μm was significantly increased all in Control Examples 1–4.

On the other hand, when powders of Reference Examples 1, 2, 3, 4, 5 and 6 having a size of 20–250 μm for 90% by weight or more thereof prepared by mechanically mixing beclometasone dipropionate having a size of 20–50 μm with hydroxypropyl cellulose, hydroxypropyl methyl cellulose, methyl cellulose, hydroxyethyl cellulose, sodium carboxymethyl cellulose and sodium carboxymethyl hydroxyethyl cellulose having a size of 20–250 μm for 90% by weight thereof, respectively, and powders of Reference Examples 7, 8, 9, 10, 11 and 12 having a size of 20–250 μm for 90% by weight or more thereof prepared from the same raw material, but different operation conditions in the spray drier, of Examples 1 and 7 and Control Examples 1–4, respectively, were stored under the same conditions, no substantial changes in the particle sizes before and after the storage were observed. From the above Experiments, it is shown that, although no changes in the particle sizes were observed, irrespective of the kind of the cellulose lower alkyl ethers when stored under a humidified condition in the powder preparations having a particle size suitable for preparations for administration to nasal cavity, no change in the particle sizes were observed only when hydroxypropyl cellulose and hydroxypropyl methyl cellulose were used, among the cellulose lower alkyl ethers, in the powder preparation having a size suitable for inhalant.

Reference Experiment 2

A determination system with a cascade impactor was installed in a constant temperature and constant humidity machine (37° C./93% R.H.) for measuring the aerodynamical particle size distribution determination by a cascade impactor under the condition simulated to a human airway. To the cascade impactor, an inhalator for generating aerosol from the powder filled in a gelatin capsule by a suction air via an induction port.

The powders having the same particle size distribution were prepared by spray drying in the same manner as in Example 1 and Example 7 and Control Examples 1–4 described in the Reference Experiment 1, except that a part of the predetermined amount of beclometasone dipropionate was substituted with fluorescein. The powders thus prepared (Reference Examples 7, 8, 9, 10, 11 and 12) were filled in #3 gelatin capsules in an amount of 5 mg each and, after packaging in sealed container, the capsules were placed in the constant temperature and constant humidity machine.

From the outside of the constant temperature and constant humidity machine, sealed container was open using rubber globes and the gelatin capsules containing the powders of the Reference Examples were attached to inhalating devices. After the holes were opened in the capsules, the pump at the cascade impactor was started. Then, the cascade impactor was taken out from the constant temperature and constant humidity machine and the fluorescein on each plate was quantitatively determined by HPLC and the aerodynamical particle size was calculated. The average aerodynamical particle sizes were 2.3 $\mu$m in Reference Example 7, 2.4 $\mu$m in Reference Example 8, 6.8 $\mu$m in Reference Example 9, 5.9 $\mu$m in Reference Example 10, 7.4 $\mu$m in Reference Example 11, and 7.3 $\mu$m in Reference Example 12.

It is known that, in the average aerodynamical particle sizes in Reference Examples 7 and 8, the powders are deposited up to the secondary bronchus, while in the average aerodynamical particle sizes in Reference Examples 9–12, the powders are deposited around larynx. Thus, the fine powders according to the present invention comprising hydroxypropyl cellulose, hydroxypropyl methyl cellulose exhibited good depositionability in lungs.

We claim:

1. An ultrafine particle powder for administering a medicament to the lower airways by oral inhalation comprising cellulose lower alkyl ether wherein said cellulose lower alkyl ether is hydroxypropyl cellulose, wherein at least 80% of said powder has a particle size of from 0.5 to 10 $\mu$m and the particle powder is capable of being delivered principally to lower airways and is obtained by spray drying, wherein said cellulose lower alkyl ether is present in an amount effective to achieve sustained release of said medicament.

2. An ultrafine particle powder for inhalation according to claim 1, wherein said ultrafine particle powder for inhalation comprises 20 to 99.8% by weight of said cellulose lower alkyl ether and 0.2 to 80% by weight of said medicament, per particle thereof.

3. An ultrafine particle powder for inhalation according to claim 1 or 2, wherein said medicament is uniformly dispersed within each of the particles thereof.

4. An ultrafine particle powder for inhalation according to claim 1 or 2, wherein said medicament is selected from the group consisting of steroids, antiallergics, bronchodilators, medicaments for chemotherapy of infective diseases, antitussives, elastase inhibitors, antineoplastic medicaments, cardiovascular medicaments, physiologically active peptide proteins and vaccines.

5. A method for administering a medicament to the lower airways comprising orally inhaling an ultrafine particle powder comprising cellulose lower alkyl ether wherein said cellulose lower alkyl ether is hydroxypropyl cellulose and hydroxypropyl methyl cellulose, and a medicament, wherein at least 80% of said powder has a particle size of from 0.5 to 10 $\mu$m, and wherein said powder is obtained by spray drying, wherein said lower cellulose alkyl ether is present in an amount effective to achieve sustained release of said medicament.

6. The method for administering a medicament according to claim 5, wherein said ultrafine particle powder comprises 20 to 99.8% by weight of said cellulose lower alkyl ether and 0.2 to 80% by weight of said medicament, per particle thereof.

7. The method for administering a medicament according to claim 5, wherein said medicament is uniformly dispersed within each of the particles thereof.

8. The method for administering a medicament according to claim 5, wherein said medicament is selected from the group consisting of steroids, antiallergics, bronchodilators, medicaments for chemotherapy of infective diseases, antitussives, elastase inhibitors, antineoplastic medicaments, cardiovascular medicaments, physiologically active peptide proteins and vaccines.

* * * * *

UNITED STATES PATENT AND TRADEMARK OFFICE
CERTIFICATE OF CORRECTION

PATENT NO.  : 5,972,388
DATED       : October 26, 1999
INVENTOR(S) : Kiyoyuki Sakon, et. al.

It is certified that error appears in the above-identified patent and that said Letters Patent is hereby corrected as shown below:

On the Cover Page, in section [54], change

"ULTRAFINE PARTICLE POWER FOR INHALATION AND METHOD FOR PRODUCTION THEREOF" to

-- ULTRAFINE PARTICLE POWDER FOR INHALATION AND METHOD FOR PRODUCTION THEREOF --.

On the Cover Page, in section [63], change

"Continuation of application No. 08/193,181, filed as application No. PCT/JP93/00786, Feb. 12, 1993, abandoned.", to -- Continuation of Application No. 08/193,181, filed February 14, 1994 (now abandoned); which is a 371 of PCT/JP93/00786, filed June 11, 1993. --.

Signed and Sealed this

Twelfth Day of September, 2000

*Attest:*

Q. TODD DICKINSON

*Attesting Officer*      *Director of Patents and Trademarks*